United States Patent [19]

Calabra et al.

[11] Patent Number: 4,999,165
[45] Date of Patent: Mar. 12, 1991

[54] PRESSURE VESSEL WITH IMPROVED GASKET VALVE

[75] Inventors: Daniel Calabra, Pittsford; Charles O. Hancock, Fairport; Brian Avant, Rochester, all of N.Y.

[73] Assignee: MDT Corporation, Torrance, Calif.

[21] Appl. No.: 428,194

[22] Filed: Oct. 27, 1989

[51] Int. Cl.⁵ ............................................. G05D 16/06
[52] U.S. Cl. .................................... 422/113; 422/117; 422/118; 422/115; 422/295; 422/296; 436/1
[58] Field of Search ............... 422/113, 117, 118, 115, 422/295, 296; 436/1

[56] References Cited

U.S. PATENT DOCUMENTS 3,694,962 10/1972 McDonald et al.
4,426,358 1/1984 Johansson ........................... 422/296
4,752,445 6/1988 Zell .................................... 422/113

Primary Examiner—David L. Lacey
Assistant Examiner—Abanti B. Singla
Attorney, Agent, or Firm—Trask, Britt & Rossa

[57] ABSTRACT

The disclosed pressurized vessel has a door seal which is pressurized by a steam supply. A diaphragm actuated solenoid valve is connected between the steam supply and the door seal. The diaphragm solenoid valve precludes the door seal from depressurizing unless the pressure within the vessel is within a preselected pressure tolerance. Also, a check valve is provided to preclude the door seal from completely depressurizing if the pressure at the steam supply is interrupted.

19 Claims, 1 Drawing Sheet

PRESSURE VESSEL WITH IMPROVED GASKET VALVE

BACKGROUND OF THE INVENTION

1. Field

The present invention relates to a pressurized vessel, such as a sterilizer, having a pressurized door seal. The invention is more particularly directed to such a vessel having means for precluding the door seal from being depressurized when pressure is not within a preselected pressure tolerance.

2. State of the Art

In a pressure vessel, such as a sterilizer, the interior of the vessel is typically subjected to a "cycle" or sequence of steps which may involve pressurization and/or evacuation. A problem area for such vessels is the sealing of the door, both before, during, and after the prescribed cycle. It is important that the door remain sealed during the cycle to avoid explosive equalization of pressure between the chamber and the environment and to avoid the escape of undesirable gases from the chamber.

One system that has been used to seal the doors of pressure chambers is an inflatable gasket, sometimes referred to as a balloon gasket. The balloon gasket is positioned around the perimeter of the entry to the chamber. Once the door is closed, the balloon gasket is inflated to create a positive seal between the door and the vessel.

In another system, an annular gasket is positioned in an annular channel around the perimeter of the entry of the chamber. A fluid-tight gasket chamber is defined between the gasket and an interior surface of the gasket channel. This gasket chamber is pressurized to force the sliding gasket into contact with the door. After the cycle is complete, the pressure behind the sliding gasket may be reduced to below atmospheric to draw the gasket away from the door to preclude the gasket from being stuck to the door when the door is opened. Such a pressurized sliding gasket system is disclosed in U.S. Pat. No. 3,694,962 (McDonald et al.), the disclosure of which is incorporated herein by this reference.

In such sliding-gasket systems, the chamber behind the gasket is typically pressurized by a steam supply. The steam supply may also be used as a sterilizing agent within the pressure chamber or sterilizer. The steam supply is typically connected to the gasket chamber by means of a three-port solenoid valve. In an energized condition, the solenoid valve connects the steam supply to the gasket chamber. When the solenoid is de-energized, the valve connects the gasket chamber line to an ejector. The ejector reduces pressure from the gasket chamber below atmospheric to draw the gasket away from the door to positively break the seal with the door.

A problem that exists in any pressurized sealing system is that if electrical power is interrupted to the valve providing pressure to the seal, the seal may be rapidly depressurized. If such depressurization occurs while a pressure or vacuum still exists within the pressure vessel, a rapid equalization of pressure can occur, which may involve sterilizing steam or gas being ejected from the pressure vessel. Such occurrences can be dangerous to personnel in the vicinity of the pressure vessel and destructive to the gasket or sealing member.

If the seal is pressurized by a steam supply, because of pressure and temperature conditions in the gasket chamber, a great deal of condensation can occur. It is not uncommon for the gasket chamber in a sliding gasket system to be completely filled with water. To bleed off condensate in the gasket chamber and the respective lines leading from the steam supply, a steam trap is typically connected between the steam supply and the solenoid valve. Such steam traps are designed to allow liquid water to drain without the loss of substantial amounts of steam pressure. However, if the steam supply is disrupted, pressure in the gasket chamber may be slowly bled off through the steam trap to thus depressurize the gasket chamber. Although the depressurization is not as rapid as occurs upon failure of power to the solenoid, such depressurization, if it occurs while pressure or vacuum still exists within the vessel or sterilizer, can cause dangerous or explosive conditions.

Thus, there remains a need for a pressure vessel having a valving configuration which eliminates dangerous conditions that can result upon disruptions to gasket pressurization while the vessel or sterilizer remains either pressurized or evacuated.

SUMMARY OF THE INVENTION

A pressure vessel of the invention includes an opening and is adapted to have its interior pressurized. A door is associated with the vessel to operate between an open and a closed position at the opening of the vessel. A seal means is associated with the vessel at the opening and is adapted to be pressurized to effect an airtight seal between the door and the vessel. A switching means is communicatively linked with the seal means. A pressure supply is also communicatively linked with the switching means. In addition, a vent means is communicatively linked with the switching means. A pressure sensing means is communicatively linked with the interior of the vessel and is associated with the switching means. The switching means is configured and adapted to have a first condition in which the pressure supply is connected to the seal means and a second condition in which the seal means is connected to the vent means. The switching means is further adapted to switch from its first condition to its second condition only when pressure within the vessel is within a preselected pressure tolerance.

The seal means typically includes a continuous gasket channel associated with the vessel and positioned at the opening. A continuous flexible gasket may readily be positioned in sliding engagement with such a gasket channel. The gasket channel and the gasket are mutually configured and adapted to provide a fluid-tight gasket chamber between the gasket and an inner surface of the gasket channel. A useful switching means is a solenoid-operated valve. A typical pressure sensing means includes a pressure sensitive diaphragm.

A pressure relief valve may be communicatively linked between the pressure supply and the switching means. It is desirably configured and adapted to expel fluid (i.e., liquid, gas, and/or vapor) when the pressure at the seal means is greater than a preselected maximum value. A pressurized steam supply may be used both to pressurize the interior of the pressure vessel and to drive the switching means.

Pressurized vessels and valving configurations of the invention eliminate many of the hazards of currently known systems. If an interruption of power or some malfunction occurs at the switching means, which may be, for example, a solenoid-operated valve, the pressure sensing means and the switching means preclude rapid depressurization of the seal means. In embodiments

DETAILED DESCRIPTION OF THE ILLUSTRATED EMBODIMENT

Figure 1:
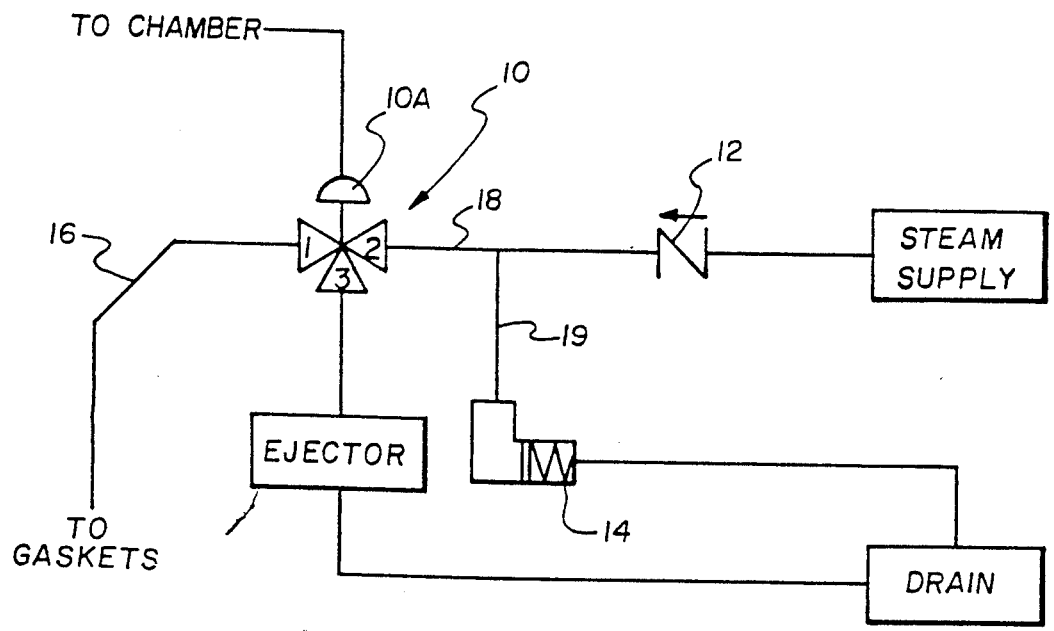
FIG. 1 is a schematic illustration of a door gasket valving configuration of the invention.

Referring to FIG. 1, a gasket valve configuration of the invention includes a diaphragm solenoid valve generally indicated at 10, a check valve 12, and a pressure relief valve 14. Valve 10 is connected to a gasket chamber (hereinafter described) by means of fluid line 16 at port 1 of valve 10, as shown, and to check valve 12 by means of fluid line 18. Pressure relief valve 14 is connected to fluid line 18 by means of fluid line 19.

Figure 2:
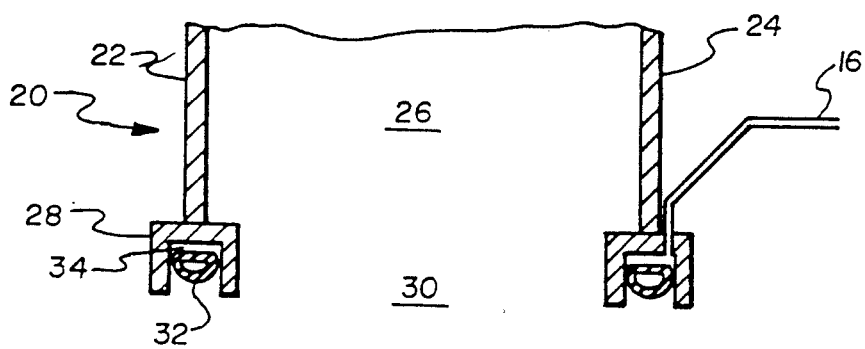
FIG. 2 is schematic sectional view of a pressure vessel of the invention having a pressurized gasket with the gasket in a retracted position.
Figure 3:
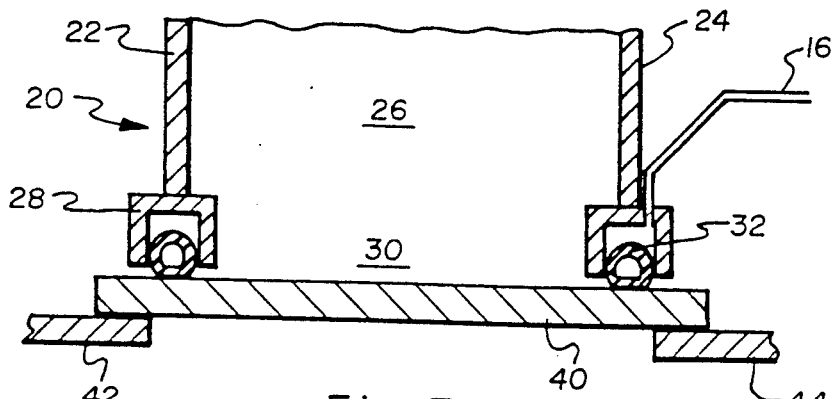
FIG. 3 is a schematic sectional view of the pressure vessel of FIG. 2 with a door in a closed position and the gasket in a sealed position.

Referring to FIGS. 2 and 3, a pressure vessel is shown in partial section view and generally indicated at 20. Vessel 20 may be, for example, a sterilizer such as the vessel disclosed in U.S. Pat. No. 3,694,962 (McDonald et al.). Vessel 20 defines an interior cavity 26. The exterior walls of vessel 20, such as walls 22 and 24, are preferably formed of a strong, rigid material such as steel. Connected to the walls of chamber 20 is a continuous annular channel 28, having a generally "U"-shaped cross-section, as shown, to define the perimeter of the entry 30 of vessel 20.

Disposed within channel 28 is a continuous seal member or gasket 32 which may be of silicon rubber, ethylene propylene, or other suitable material to withstand high and low external pressures and wide ranging temperatures of sterilization. Seal member 32 may be of any appropriate cross-section, but is preferably circular, and is preferably hollow. Seal member 32 slidably engages with the interior of channel 28 to define a fluid-tight chamber 34 between the seal member 32 and the interior of channel 28. Communicating with gasket chamber 34 about opening 30 along channel 28 at one or more points are one or more pressure lines 16, which are in turn connected to port 1 of valve 10 (FIG. 1).

Referring to FIG. 3, a door or closure member 40 may be positioned by various means proximate channel 28 to be contacted by sealing member 32. Door 40 may be associated with vessel 20 by means of a hinged or sliding relationship or any other appropriate mechanism. Some form of locking mechanism, schematically represented by locking plates 42 and 44, are used to lock door 40 in position with respect to channel 28. Locking members 42 may be, for example, sliding or pivoting lock members, or fixed stop or clamp members, or some combination of these mechanisms.

With the door in an open position, removed from entry 30 as shown in FIG. 2, articles may be placed in the interior 26 of vessel 20 through entry 30. In this position, seal member 32 is in the position shown in FIG. 2, drawn back into channel member 28 and away from the channel opening.

Once the vessel is loaded, the door is moved into its closed position as shown in FIG. 3, either manually or by any suitable drive mechanism. In the closed position, and with the locking mechanism securing door 40 in its closed position, the solenoid in valve 10 is energized to connect port 1 to port 2 to allow pressurized fluid, in this case steam, to enter line 16 from valve 10 to pressurize chamber 34. The pressure in chamber 34 forcibly slides seal member 32 toward door 40 into a sealing relationship with door 40. In this configuration, the vessel is sealed and may be pressurized or evacuated.

Once the sterilizing cycle is complete, valve 10 is operated to connect port 1 with port 3 to thereby connect the ejector to line 16. The ejector produces a subatmospheric pressure, i.e., below atmospheric pressure, in line 16. This subatmospheric pressure in chamber 34 forcibly draws seal member 32 away from door 40 and back into its position shown in FIG. 2, to break the seal with the door 40. With the seal thus broken, door 40 may be slid or otherwise moved from opening 30 to permit removal of the sterilized article.

The association between channel 28, gasket 32, and line 16 constitutes a pressurized seal means. Other forms of pressurized seal means may also be employed for use with the valving configuration described hereinafter. For example, a pressurized balloon gasket may also be used. However, it is believed that a pressurized sliding gasket is preferable.

Valve 10 is provided with a diaphragm 10A which is connected by means of a fluid line, as shown, to the interior of the pressure vessel or sterilizer. Diaphragm 10A senses the pressure within vessel 20. Valve 10 is constructed so that even if power is lost to valve 10 so that the solenoid is de-energized, it will not switch from connecting port 1 to port 3 unless the pressure within vessel 20 is within a certain tolerance to atmospheric pressure. In the preferred embodiment, valve 10 will not connect port 1 to port 3 unless diaphragm 10A senses a pressure in vessel 20 within 2 pounds per square inch of atmospheric pressure (PSIA). A suitable valve for such use may be purchased from Asco Corporation of N.J. Thus, if power is lost to solenoid valve 10, gasket chamber 34 is not allowed to depressurize to cause dangerous or explosive equalization of pressure, unless the pressure within vessel 20 is within the prescribed pressure tolerance.

Another dangerous condition can exist when the steam supply is interrupted, independent of any interruption of power to solenoid valve 10. In other systems, a steam trap exists in the position of pressure relief valve 14. Because of pressure conditions in gasket chamber 34, line 16, line 18, and line 19, these lines can be filled with water rather than steam. A steam trap is typically provided at the position of pressure relief valve 14, to allow condensed water to escape, with only minimal amounts of steam or air escaping. However, if an interruption of the steam supply were to occur, pressure in line 16 and chamber 34 will eventually deteriorate. Such deterioration of pressure has been known to occur in approximately one minute. Depressurization can occur while pressure or vacuum still exists within the interior 26 of vessel 20, causing dangerous or explosive pressure equalizations.

In the illustrated embodiment, a pressure relief valve 14 is provided to allow water, steam, or air to escape when the pressure in line 19 exceeds a preselected value. A preferred value for such pressure relief is 75 PSIA. Thus, even if the steam supply is interrupted, the association of check valve 12 and pressure relief valve 14 maintains the pressure in gasket chamber 34 to at least 75 PSIA. This system reduces the chance of an explosive equalization of pressure between the vessel 20 pressure and the atmospheric pressure. A suitable valve 14 may be purchased from Conbraco, part number 16-201-02, 75 PSIG.

It has been assumed that condensed water within chamber 34 or its associating lines was to be avoided. Because water or other liquids are only slightly compressible, water has less ability to absorb pressure changes within gasket chamber 34 caused by pressurization, or, particularly, evacuation of the interior 26 of vessel 20. Upon evacuation, if the chamber 34 were filled with water, the volume of chamber 34 would be essentially constant. Thus, steam traps are commonly provided for the purpose of reducing the amount of water buildup, due to condensation, in chamber 34. However, with the provision of a pressure relief valve, such as valve 14, it is not believed that water buildup within chamber 34 precludes the system from properly functioning. If the pressure, either hydrostatic or dynamic, in chamber 34 exceeds 75 PSIA, such pressure is allowed to be reduced by means of pressure relief valve 14.

Thus, with the provision of solenoid diaphragm valve 10 and pressure relief valve 14, dangerous conditions incident to either a failure of power at solenoid valve 10 or loss of steam pressure due to a failure of the steam supply, are avoided.

Reference herein to details of the illustrated embodiment are not intended to limit the scope of the appended claims, which themselves recite those features considered important to the invention.

We claim:

1. A pressure chamber, comprising:
   a vessel configured to have an opening and an interior adapted to be pressurized;
   a door positioned and arranged with respect to said vessel to operate between an open and closed position at said opening;
   seal means positioned and arranged with respect to said vessel at said opening and constructed so as to be pressurized to effect an airtight seal between said door and said vessel;
   switching means communicatively linked with said seal means;
   a pressure supply communicatively linked with said switching means;
   vent means communicatively linked with said switching means; and
   pressure sensing means communicatively linked with the interior of said vessel and associated with said switching means;
   wherein said switching means is configured and adapted to have a first condition in which said pressure supply is connected to said seal means and a second condition in which said seal means is connected to said vent means;
   said switching means being further constructed so as to only switch from said first condition to said second condition when pressure within said vessel is within a preselected pressure tolerance.

2. A pressure chamber according to claim 1 wherein said seal means includes:
   a continuous gasket channel communicated at said opening; and
   a continuous flexible gasket positioned in sliding engagement within said gasket channel;
   said gasket channel and said gasket being mutually configured and constructed so as to provide a fluid-tight gasket chamber between said gasket and an inner surface of said gasket channel, said gasket chamber being in communication with said switching means.

3. A pressure chamber according to claim 1 wherein said switching means is a solenoid.

4. A pressure chamber according to claim 3 wherein said pressure sensing means includes a pressure-sensitive diaphragm.

5. A pressure chamber according to claim 4 wherein said vent means comprises a pressure relief valve linked between said pressure supply and said switching means, said pressure relief valve being configured and constructed so as to expel fluid when the pressure at said seal means is greater than a preselected maximum value.

6. A pressure chamber according to claim 1 wherein said pressure supply is a pressurized steam supply.

7. A pressure chamber according to claim 6 wherein said pressurized steam supply is in flow communication with the interior of said vessel so as to pressurize the interior of said vessel.

8. In a pressurized vessel having an interior and a pressurized seal means for effecting a seal between an entry of said vessel and a door positioned at said entry, said seal means being pressurized by a pressure supply, and a switching means for selectively switching between a first condition to provide fluid communication between said pressure supply and said seal means and a second condition to provide fluid communication between said seal means and a relief vent, the improvement comprising:
   a pressure sensing means associated with said switching means and communicatively linked with the interior of said vessel;
   said switching means being constructed so as to preclude switching from said first condition to said second condition when higher than a preselected pressure exists within the interior of said vessel.

9. A vessel according to claim 8 wherein said seal means includes:
   a continuous gasket channel positioned to be arranged with said entry of said vessel;
   a flexible continuous gasket positioned in said gasket channel and configured and constructed so as to be in an airtight and sliding engagement with said gasket channel;
   said gasket channel and being mutually configured and constructed so as to provide a gasket chamber between said gasket and the interior of said gasket channel, said gasket chamber being in communication with said switching means.

10. A vessel according to claim 9 wherein said switching means is a solenoid-operated valve.

11. A vessel according to claim 10 wherein said pressure sensing means includes a pressure sensitive diaphragm.

12. A vessel according to claim 9 comprising the further improvement of:
   a pressure relief valve being communicatively linked between said pressure supply and said seal means and being constructed so as to expel fluid to maintain the pressure within said gasket chamber under a maximum preselected value.

13. A vessel according to claim 8 wherein said pressure supply comprises pressurized steam.

14. A combination of a pressurized vessel and a plumbing system having a pressurized seal system, a pressure supply and a relief vent, said combination comprising:

a switching means for switching between ports, said switching means including:

a first port communicatively linked to said seal system;

a second port associated with said first port and communicatively linked to said pressure supply;

a third port associated with said first port and communicatively linked to said relief vent;

wherein said switching means has a first condition in which said first port is communicatively linked with said second port, said third port being closed, and a second condition in which said first port is connected to said third port, said second port being closed; and a pressure sensing means associated with said switching means and communicatively linked with the interior of said vessel;

said switching means constructed and arranged so as to switch from said first condition to said second condition only when the pressure in said pressurized vessel is within a preselected pressure tolerance.

15. A combination of a pressurized vessel and a plumbing system according to claim 14 wherein said switching means includes a solenoid-operated valve.

16. A combination of a pressurized vessel and a plumbing system according to claim 15 wherein said pressure sensing means includes a pressuresensitive diaphragm.

17. A combination of a pressurized vessel and a plumbing system according to claim 15, further comprising a pressure relief valve constructed so as to expel fluid when the pressure at said second port is greater than a preselected amount.

18. A combination of a pressurized vessel and a plumbing system according to claim 17 wherein said pressure supply comprises pressurized steam.

19. A combination of a pressurized vessel and a plumbing system according to claim 18 wherein said vessel is in flow communication with said pressure supply so as to pressurize said vessel by said pressure supply.

* * * * *

UNITED STATES PATENT OFFICE
CERTIFICATE OF CORRECTION

Patent No. 4,999,165     Dated MARCH 12, 1991

Inventor(s) CALABRA ET AL.

It is certified that error appears in the above-identified patent and that said Letters Patent is hereby corrected as shown below:

In claim 3, after "solenoid" and before "." insert -- -operated valve--.

Signed and Sealed this

Twenty-eighth Day of July, 1992

Attest:

DOUGLAS B. COMER

*Attesting Officer*     *Acting Commissioner of Patents and Trademarks*